(12) United States Patent
Maitland et al.

(10) Patent No.: US 12,076,464 B2
(45) Date of Patent: Sep. 3, 2024

(54) DRUG ELUTING SHAPE MEMORY FOAM

(71) Applicant: The Texas A&M University System, College Station, TX (US)

(72) Inventors: Duncan Maitland, College Station, TX (US); Corey Bishop, Landsdale, PA (US); Shreedevi Arun Kumar, College Station, TX (US)

(73) Assignee: The Texas A&M University System, College Station, TX (US)

( * ) Notice: Subject to any disclaimer, the term of this patent is extended or adjusted under 35 U.S.C. 154(b) by 964 days.

(21) Appl. No.: 17/072,166

(22) Filed: Oct. 16, 2020

(65) Prior Publication Data
US 2021/0113741 A1  Apr. 22, 2021

Related U.S. Application Data

(60) Provisional application No. 62/916,515, filed on Oct. 17, 2019.

(51) Int. Cl.
| | |
|---|---|
| *A61L 27/56* | (2006.01) |
| *A61L 27/18* | (2006.01) |
| *A61L 27/54* | (2006.01) |
| *C08G 18/32* | (2006.01) |
| *C08G 18/34* | (2006.01) |
| *C08G 18/38* | (2006.01) |
| *C08G 18/73* | (2006.01) |
| *C08G 101/00* | (2006.01) |

(52) U.S. Cl.
CPC ............ *A61L 27/56* (2013.01); *A61L 27/18* (2013.01); *A61L 27/54* (2013.01); *C08G 18/3206* (2013.01); *C08G 18/341* (2013.01); *C08G 18/3825* (2013.01); *C08G 18/73* (2013.01); *A61L 2300/626* (2013.01); *A61L 2300/802* (2013.01); *A61L 2400/16* (2013.01); *C08G 2101/00* (2013.01); *C08G 2280/00* (2013.01)

(58) Field of Classification Search
CPC .................................................... A61L 27/54
See application file for complete search history.

(56) References Cited

U.S. PATENT DOCUMENTS

| | | | |
|---|---|---|---|
| 6,090,996 A | 7/2000 | Li | |
| 6,656,488 B2 | 12/2003 | et al. | |
| 8,092,779 B2 | 1/2012 | Chernomorsky et al. | |
| 8,303,625 B2 | 11/2012 | Lendlein et al. | |
| 10,265,433 B2 | 4/2019 | Maitland et al. | |
| 2003/0055198 A1 | 3/2003 | Langer et al. | |
| 2003/0170308 A1* | 9/2003 | Cleary | A61K 8/73 424/487 |
| 2004/0254625 A1 | 12/2004 | Stephens et al. | |
| 2009/0198321 A1 | 8/2009 | Sutermeister et al. | |
| 2013/0110066 A1 | 5/2013 | Sharma et al. | |
| 2014/0112990 A1* | 4/2014 | Bencherif | A61P 37/02 424/277.1 |
| 2015/0335783 A1 | 11/2015 | Kohn et al. | |
| 2016/0270961 A1* | 9/2016 | Maitland | A61L 15/18 |
| 2017/0002130 A1 | 1/2017 | Singhal et al. | |
| 2019/0015108 A1 | 1/2019 | Maitland et al. | |
| 2019/0192743 A1 | 6/2019 | Maitland et al. | |
| 2019/0209730 A1 | 7/2019 | Maitland et al. | |
| 2020/0017625 A1 | 1/2020 | Nash et al. | |

FOREIGN PATENT DOCUMENTS

WO  WO2003071991  9/2003

OTHER PUBLICATIONS

Choi et al. Fabrication of Oxygen Releasing Scaffold by Embedding H2O2-PLGA Microspheres into Alginate-Based Hydrogel Sponge and Its Application for Wound Healing. Appl. Sci. 2018, 8, 1492. Aug. 29, 2018. (Year: 2018).*
Hamilton Needle Gauge Chart. https://www.hamiltoncompany.com/laboratory-products/needles-knowledge/needle-gauge-chart. As viewed on Oct. 11, 2023. (Year: 2023).*
International Searching Authority, "Notification of Transmittal of the International Search Report and the Written Opinion of the International Searching Authority," mailed Jan. 6, 2021, in International application No. PCT/US2020/055891.
Todd R. Hoare, et al., Science Direct, "Hydrogels in drug delivery: Progress and challenges," 2008, 15 pages.
Ya-Yen Yu, et al., "The effect of moisture absorption on the physical properties of polyurethane shape memory polymer foams," 2011, 7 pages.
Mathilde Champeau, et al., "Current manufacturing processes of drug-eluting sutures," 2017, 12 pages.
Tao Xie, "Recent advances in polymer shape memory," Elsevier Ltd., 2011, 16 pages.
Landon D. Nash, et al., "Increased X-ray Visualization of Shape Memory Polymer Foams by Chemical Incorporation of Iodine Motifs," 2017, 16 pages.
Samer Tohme, et al., "Surgery for Cancer: A Trigger for Metastases," 2017, 10 pages.
Jianyu Li, et al., "Designing hydrogels for controlled drug delivery," 2016, 38 pages.
Business Wire, businesswire.com, "Shape Memory Medical Receives FDA Clearance for the IMPEDE® FX Embolization Plug," May 28, 2019, 2 pages.

(Continued)

*Primary Examiner* — Stephen E Rieth
(74) *Attorney, Agent, or Firm* — Trop, Pruner & Hu, P.C.

(57) ABSTRACT

Tumor resection is commonly practiced to prevent the progression of cancer. However, there are post-surgery concerns including the formation of a void that can allow cancer cells to escape at the surgery site, which increases the risk of metastasis. To counter this challenge, an embodiment includes a polyurethane-based shape memory foam as a tissue void-filling device that can also release anti-cancer drugs. Such foams may activate at body temperature and become malleable. Such properties may enable the foam to be shaped to precisely seal the tissue void and then serve as a drug-eluting device. Based on the drug composition with poly vinyl alcohol (PVA), the drug release profile from the foam may be altered depending on the application.

21 Claims, 4 Drawing Sheets

(56) References Cited

OTHER PUBLICATIONS

Pooja Singhal, et al., "Controlling the Actuation Rate of Low-Density Shape-Memory Polymer Foams in Water," 2013, 11 pages.
Basicmedical Key, basicmedicalkey.com, "Viscosity-Inducing Agents", 9 pages.
European Patent Office, Extended European Search Report dated Octoer 6, 2023 in European Patent Application No. 20877997.5 (5 pages).

\* cited by examiner

DRUG ELUTING SHAPE MEMORY FOAM

CROSS-REFERENCE TO RELATED APPLICATION

This application claims priority to U.S. Provisional Patent Application No. 62/916,515 filed on Oct. 17, 2019 and entitled "Drug Eluting Shape Memory Foam", the content of which is hereby incorporated by reference.

TECHNICAL FIELD

Embodiments of the invention are in the field of medical devices.

BACKGROUND

Cancer is the second leading cause of mortality and is estimated to cause deaths of ~600,000 people in 2019 in the United States alone. For solid tumors, one of the primary medical interventions includes surgery where the tumor is resected along with a portion of the surrounding tissue to ensure that there are no cancer cells left behind. However, salvaging normal tissue is critical in vital organs like lungs and there is currently no accurate detection method to predict the boundary of cancer cells. This could potentially result in retention of cancer cells that will later be responsible for cancer recurrence. In addition, studies have linked the possibility of increased occurrence of metastasis through a) the tissue void that exists after resection through which the cancer cells can escape, or b) post-operative stress. Conventionally the tissue void is sutured after surgery by using biodegradable or non-degradable sutures. There are several challenges associated with the suture approach including complications associated with ineffective wound healing and suture removal for non-dissolvable sutures. In the case of dissolvable sutures, degradation rate can be accelerated depending on the physiological conditions of the patient. For example, if the patient has a high fever then the sutures are more likely to degrade faster than the predicted timeline possibly leading to improper wound healing.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

Figure 1:
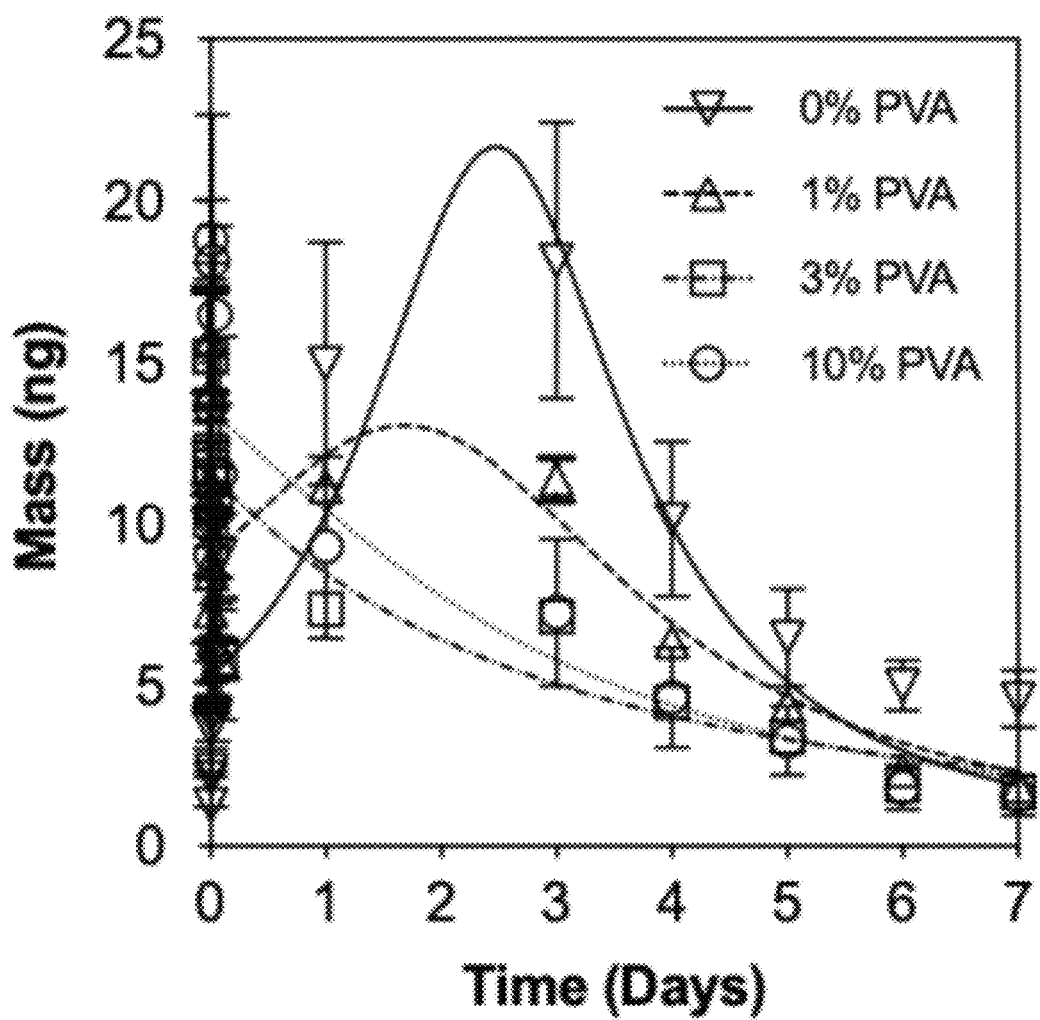
FIG. 1 includes a non-cumulative release curve for an embodiment of the invention.
Figure 2:
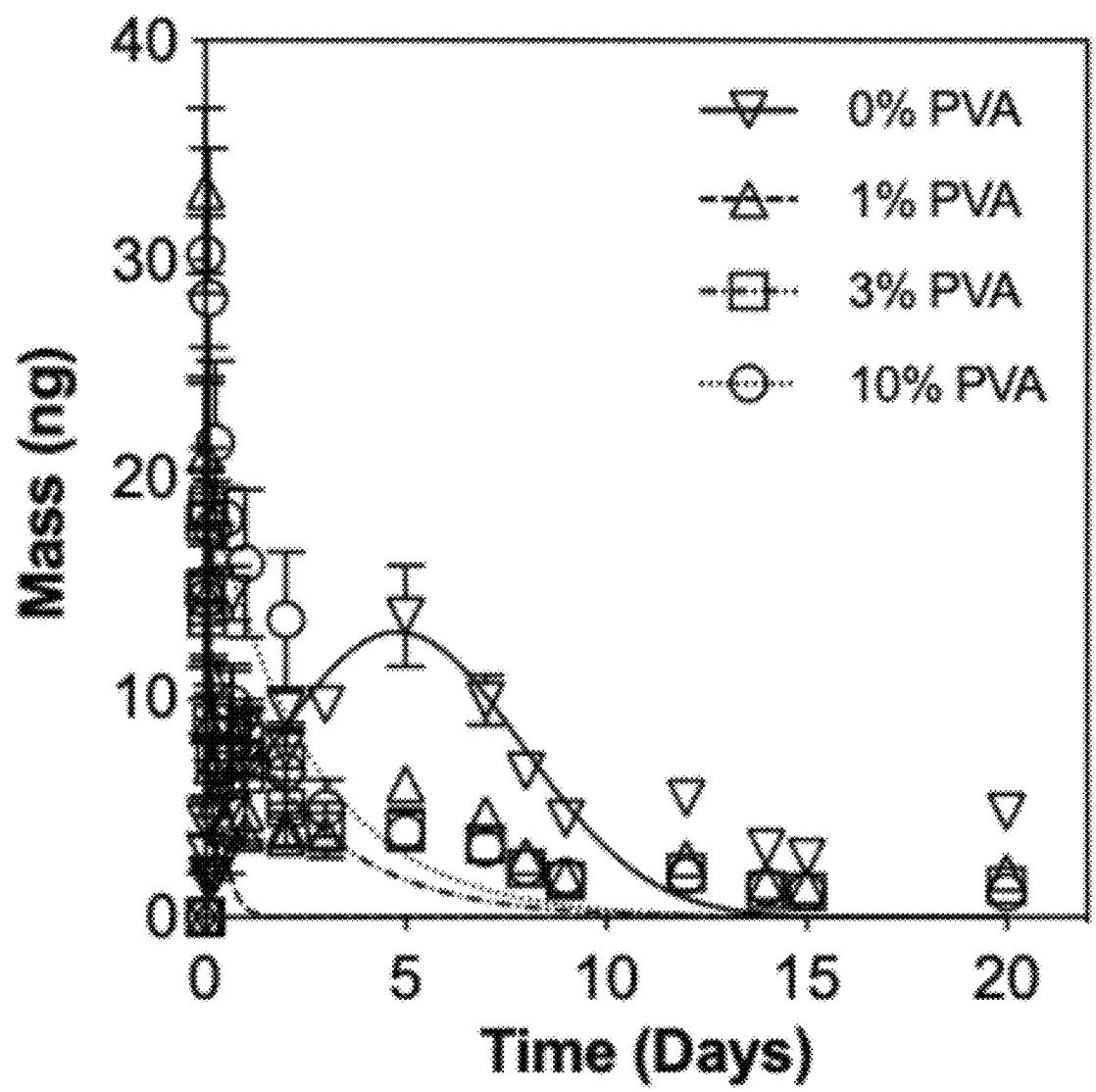
FIG. 2 includes a non-cumulative release curve for an embodiment of the invention.
Figure 3:
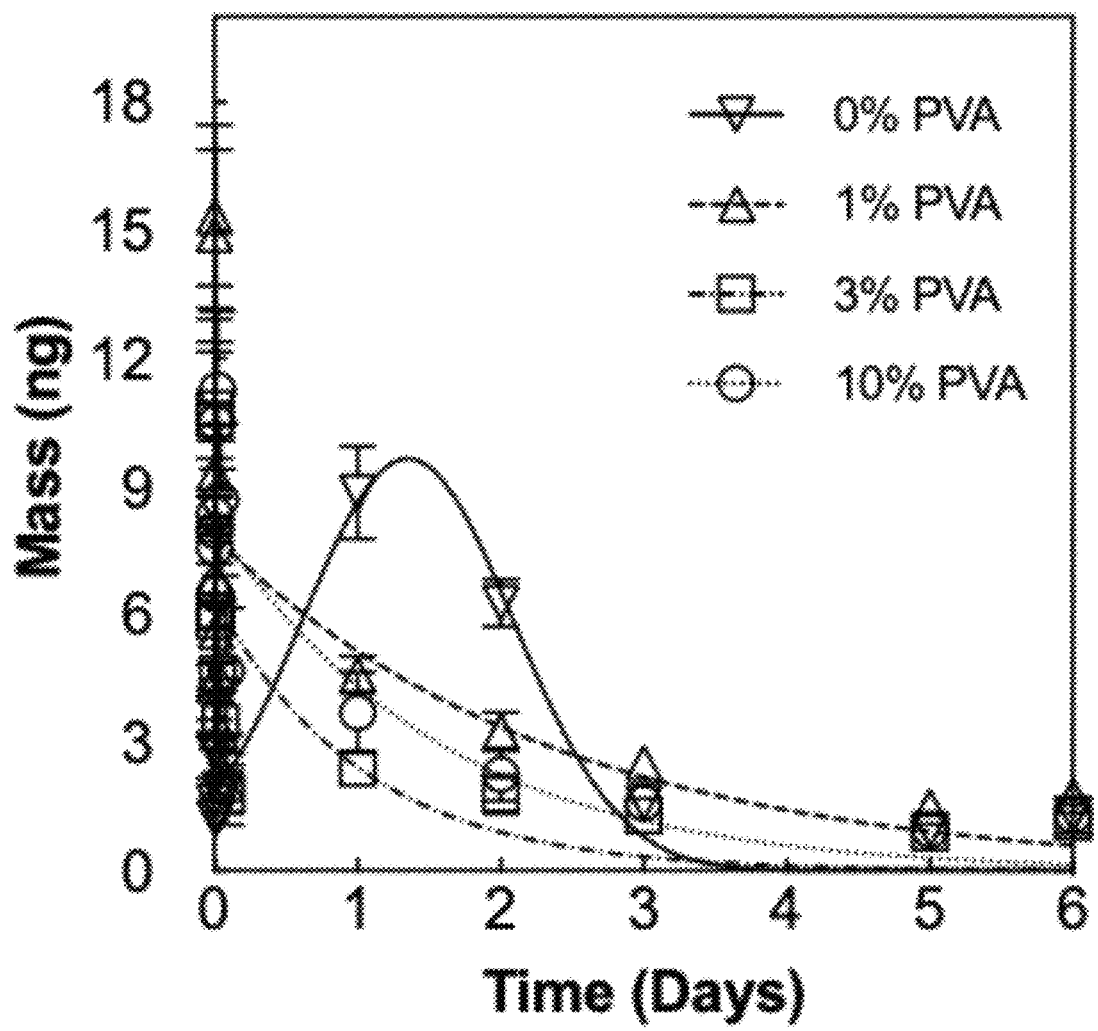
FIG. 3 includes a non-cumulative release curve for an embodiment of the invention.

The Y-axis of FIGS. 1-3 depicts the mass of an agent that has eluted from a foam.

Figure 4:
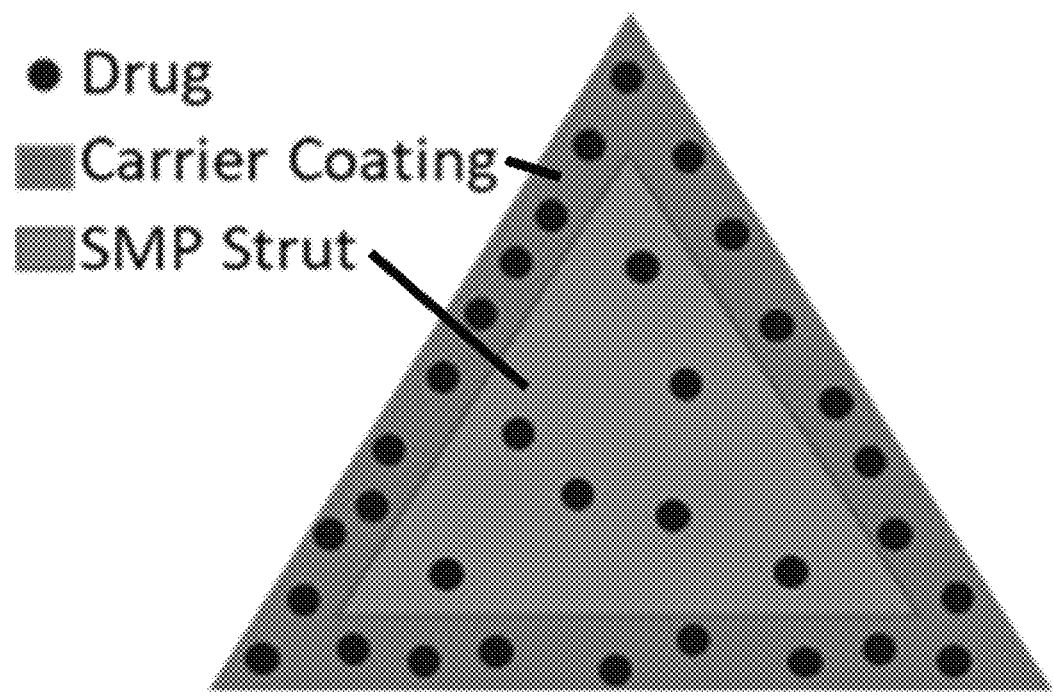

FIG. 4 includes a cross-section of a shape memory polymer foam strut in an embodiment of the invention.

DETAILED DESCRIPTION

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments (e.g., walls may not be exactly orthogonal to one another in actual fabricated devices). Moreover, the drawings may only show the structures useful to understand the illustrated embodiments. Additional structures known in the art may not have been included to maintain the clarity of the drawings. For example, not every layer of a device is necessarily shown. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Phrases such as "comprising at least one of A or B" include situations with A, B, or A and B.

To address the above issues, biodegradable sutures have been widely used to close the wound after surgery. There have also been efforts to use the sutures as a drug delivery system. However, Applicant determined few drug-eluting sutures have been clinically translatable due to a number of challenges including non-optimal mechanical strength of the sutures and an inability to achieve sustained drug release. Applicant further determined poor control over the drug release from the sutures (or even the ability to load the drug into the suture) further results in compromised therapeutic efficacy. Sutures are often dipped in the drug solution resulting in immediate uncontrolled release of the drug. Drug residence time in the body is thus far less to achieve the desired therapeutic effect. Applicant determined another major concern relating to absorbable sutures is the increased inflammation. In the context of tumor resection, sutures often do not foster precise sealing of the wounds. Thus, area of the wound that is not in contact with the suture might pave the way for the residual cancer cells to escape.

An alternative to sutures is post-operative biodegradable implants such as, for example, hydrogels. Hydrogels have been extensively characterized for their ability to enable drug release. Hydrogels can be engineered to be responsive to various stimuli including temperature and pH further releasing cargo. For example, tumor microenvironments tend to have lower pH compared to the physiological pH. Hydrogels can be chemically engineered to be sensitive to low pH environment leading to preferentially delivery of the cargo in the tumor microenvironment. Although this is a theoretically effective alternative to drug-eluting sutures for controlled drug delivery, Applicant determined hydrogels do not possess adequate tensile strength to enable precise control over the timing of drug release or sealing of the wound. Increased water content in the hydrogels yields a non-rigid and liquid-like structure making hydrogels an ineffective solution to precisely plug tissue voids. This mechanical property also causes premature dissolution of the device resulting in non-controlled release of the cargo load.

In light of the above, Applicant determined there is a need for a platform to more precisely seal the tissue void while therapeutically impeding the development of metastasis.

To that end, an embodiment includes a SMP foam that can be used to fit a void based on the foam's SMP properties. The foam is loaded with small therapeutic molecules to promote killing residual cancel cells near the surface of the resection. Thus, such an embodiment provides advantages over conventional technologies because such a foam is biocompatible and can be loaded with drugs with tunable release profiles to prevent or slow down the recurrence of malignant diseases.

Small molecule drugs can be loaded onto or into the foams by incubating the foams with drugs in a polyvinyl alcohol (PVA) solution. Activation of the foam at body temperature can then enable release of the drugs (or a portion thereof) from the foam. Time of release can also be modulated using different percentages of PVA enabling a regulated drug-eluting device. Drug release profiles may be tuned by changing the chemical composition of the foams, the amount of PVA included with the foam, the size of cells in the foam, the degree of reticulation for cells of the foam, or combinations thereof.

An embodiment includes a tissue-void filling and drug-eluting shape memory polymer (SMP) foam. SMP foams include hexamethylene diisocyanate (HDI)-based foams. However, another embodiment includes a foam that is a reaction product of hydroxypropyl ethylenediamine (HPED), triethanolamine (TEA), and 2,2,4-trimethyl hexamethylene diisocyanate (TMHDI). TMHDI foams may have smaller pore sizes as compared to HDI foams and therefore have different drug delivery profiles.

In an embodiment Acriflavine, a fluorescent small molecule, is used as a cargo to illustrate a therapeutic agent release profile from the foam. In an embodiment, PVA is used to improve agent uptake onto or into the foam. Differential drug uptake and release profiles are achievable with reticulated, partially reticulated, and non-reticulated TMHDI-based foams or other SMP foams.

Shape-memory materials have the useful ability of being formable into a primary shape, reformable into a stable secondary shape, and then being controllably actuated to recover their primary shape. Both metal alloys and polymeric materials can have shape memory. In the case of metals, the shape-memory effect arises from thermally induced solid phase transformations in which the lattice structure of the atoms changes, resulting in macroscopic changes in modulus and dimensions. In the case of polymeric materials, the primary shape is obtained after processing and fixed by physical structures or chemical crosslinking. The secondary shape is obtained by deforming the material while it is in an elastomeric state and that shape is fixed in one of several ways including cooling the polymer below a crystalline, liquid crystalline, or glass transition temperature; by inducing additional covalent or ionic cross-linking, etc.

While in the secondary shape some or all of the polymer chains are perturbed from their equilibrium random walk conformation, having a certain degree of bulk orientation. The oriented chains have a certain potential energy, due to their decreased entropy, which provides the driving force for the shape recovery. However, they do not spontaneously recover due to either kinetic effects (if below their lower Tg) or physical restraints (physical or chemical crosslinks). Actuation occurs for the recovery to the primary shape by removing that restraint (e.g., heating the polymer above its glass transition or melting temperature, removing ionic or covalent crosslinks, etc.) Other types of polymers which undergo shape memory behavior due to photon induced conformational transformations, conformational changes (e.g., rod-coil transition) due to changes in chemical environment (pH, ionic strength, etc.), or structural changes due to imposed fields (e.g., electric, magnetic, . . . ) may also be used.

Thus, SMPs are polymeric smart materials that have the ability to return from a deformed state (temporary shape) to their original (permanent) shape induced by an external stimulus (trigger), such as temperature change. SMPs can retain two or more shapes, and the transition between those is induced by temperature. In addition to temperature change, the shape change of SMPs can also be triggered by an electric or magnetic field, light, or solvent plasticization. As well as polymers in general, SMPs also cover a wide property-range from stable to biodegradable, from soft to hard, and from elastic to rigid, depending on the structural units that constitute the SMP. SMPs include thermoplastic and thermoset (covalently cross-linked) polymeric materials.

Embodiments provide several advantages over other technologies, such as hydrogel-based technologies. An embodiment utilizes a carrier polymer that is added to the SMP foam. Applicant determined many SMP foams (without such a carrier polymer) may be unable to load a significant amount of a drug (e.g. small molecule). Water is a small molecule but Applicant has previously determined that after exposing SMP foams to differing humidity levels for varying lengths of time, the foams exhibited a maximum water uptake of 8.0% (by mass) after exposure to 100% relative humidity for 96 hours. Water is polar but it is small and many HDI and TMHDI based SMP foams are relatively hydrophilic. Thus, Applicant determined that to deliver or hold more drug, a carrier polymer could be added to the foam. However, Applicant further determined the thickness and total mass of the carrier polymer added to the foam will limit the crimping and/or shape recovery of the foam (which could limit the ability to deliver the foam via tortuous paths, such as using a catheter to deliver a foam via small and winding vasculature). Yet, Applicant determined PVA provides advantages over conventional technologies (e.g., a hydrogel) in that the shape recovery rate and diameter are not as limited as compared to those conventional technologies. Further, PVA is more tunable relative to total mass deposited than many hydrogels, so PVA may also help reduce crimping limitations caused by adding mass. A SMP foam can be controllably expanded while being held in precise placement. A SMP foam expands to its permanent shape a short period of time (e.g., a few seconds) after actuation, which is much faster than conventional hydrogel-based devices.

Applicant determined a critical point for some applications is that, for example, certain cancers may require a timed release into the local tissue. This may be due to difficulties identifying cancer margins and the inability to be confident all of the cancer was surgically removed along with a tumor. Chemotherapy and radiation are secondary methods for eliminating remaining margins and/or metastatic cells circulating in the bloodstream. However, the release rate and the dual release from the PVA and SMP are beneficial to a local and sustained delivery of anti-cancer molecules that is localized to the tumor site. The "dual release" addresses the release of therapeutic agents from both the PVA (where the PVA may be a form of shell outside the foam) and the SMP foam (where agents may be within cells of the foam with or without PVA also being in the cells).

An embodiment includes a method for creating a drug-eluting SMP foam. The method includes incubating the foam in a 0.017 mg/mL acriflavine solution (e.g., 1 mg/mL in acriflavine solution dimethyl sulfoxide (DMSO)) that is mixed with varying PVA solutions of 0%, 1%, 2%, 3%, 10% (wt./vol) overnight on a rotator at room temperature (n=3). Different PVA concentrations may be used to increase drug viscosity and drug uptake onto or into the foam. In other embodiments PVA is held constant and acriflavine concentrations are varied (which changes the PVA viscosity). Foams may then be removed from the respective drug/PVA solutions and dried in a vacuum chamber for 5 days. The foams may then be incubated in 0.4 mL phosphate-buffered saline (PBS) at 37° C. Supernatants may be removed at various time points and measured for fluorescence at 416/514 nm (Ex/Em).

| Concentration of Acriflavine (mg/mL) | Concentration of PVA (wt/vol) (%) |
|---|---|
| 0.017 | 0 |
| 0.017 | 1 |
| 0.017 | 2 |
| 0.017 | 3 |
| 0.017 | 10 |

The above table shows chemical compositions for multiple embodiments.

Increasing PVA concentration with drug solution proportionally increases the viscosity. This increased viscosity enables increased retention of drug within the foam. Other viscosity-altering compounds such as carboxymethyl cellulose can also be used (instead of or in addition to PVA) to achieve similar drug uptake and release.

In an embodiment acriflavine is used as a cargo in the free drug form (which helps illustrate the release profile for drug solutions with different PVA concentrations). Embodiments with increasing PVA concentrations have increased drug uptake onto or into the foam (see, e.g., FIGS. 1, 2, 3). This may be due, at least in part, to the increased viscosity of the drug when combined with PVA, which enables the drug to be trapped within or on the pores present in the foam. An embodiment that includes dipping the foam in drug solution without PVA (0% PVA) has less drug uptake compared to that of solutions with increasing PVA concentration. An embodiment may include depositing multiple foams to a surgical site where those foams have varying PVA content, and therefore varying release profiles (which allows one to distribute drug elution over a programmed period of time). Release profiles also vary compared to the PVA content within the drug solutions. A drug solution with 0% PVA enables a delayed burst release while solutions with higher PVA concentrations enable immediate release from the foams. This drug formulation mixed with PVA can therefore modulate drug uptake and drug release profile by tuning the PVA concentration. Notably, although an anti-inflammatory drug, acriflavine, is used in an embodiment, other drug molecules (e.g., Doxorubicin) can be loaded onto or into the foam. Many therapeutics drugs are small, hydrophobic molecules and can thus be expected to have similar loading and release profile to that of acriflavine. Such therapeutic drugs may be substituted for acriflavine or added to acriflavine in other embodiments.

Again, as mentioned above, drug release profiles can be modulated depending on the desired therapeutic effect. For example, release profiles may be altered using drug encapsulated nanoparticles instead of using unencapsulated "free drug". Drug-encapsulated vehicles (including micro- and nanoparticles and hydrogels) can enable delayed sustained release once the particles are released from the foam. Thus, the drug-eluting SMP foams can facilitate short-term and long-term drug delivery depending on the type of cargo and PVA used. The amount of drug release can also be optimized based on the stock concentration of the drug.

Regarding in vitro release of acriflavine from HDI-based SMP foams, see FIG. 1. In FIG. 1 the non-cumulative release curve indicates that acriflavine release from SMP foams increases (or at least differs) with increasing PVA concentration. This may be because of the increased loading of acriflavine that is due to PVA (and PVA's affinity for the foam). In FIG. 2 the non-cumulative release curve indicates that acriflavine release from reticulated HH80 SMP foams increased (or at least differs) with increasing PVA concentration.

Different embodiments may include different drug release profiles such as, for example, longer release time, no spike release, dual spike release, and the like. This may be performed as explained below in the claims section.

In vitro release of acriflavine from non-reticulated TMHDI 60 foam is addressed in FIG. 3. In FIG. 3 the non-cumulative release curves indicate that acriflavine release from TH60 SMP foams increased (or at least differs) with increasing PVA concentration.

Embodiments include doxorubicin-loaded SMP foams with increasing PVA concentrations, where the foams are crimped down to 0.8 mm in diameter. This size limit better enables one to inject the foam into the intraperitoneal region of the mice using an 18 G needle.

While at times SMP foams including agents included with PVA are compared with combinations of SMP foams and hydrogels, in some embodiments a foam may be coupled to PVA/agent portions as well as agents included in a hydrogel.

The following examples pertain to further embodiments.

Example 1

An apparatus comprising: a shape memory polymer (SMP) foam including open cells, the SMP foam having first and second states; and a material composition included within an open cell, the material composition including: (a) at least one therapeutic agent, and (b) at least one of Polyvinyl alcohol (PVA), carboxymethyl cellulose, or combinations thereof; wherein the at least one therapeutic agent includes at least one of a drug, a peptide, a protein, an antigen, a nucleic acid, an anesthetic, an antihistamine, antifungal agent, a vasodilator, an anti-inflammatory agent, an immunosuppressant, a growth factor, a cytokine, an interleukin, or combinations thereof.

In an embodiment the foam is a polyurethane thermoset foam. In some embodiments, the PVA is not chemically bound to the foam. In some embodiments the therapeutic agent is not chemically bound to the foam. In some embodiments the PVA is not chemically bound to the foam and the therapeutic agent is not chemically bound to the foam. In an embodiment the PVA is not chemically bound to the therapeutic agent.

Example 1.1

An apparatus comprising: a shape memory polymer (SMP) foam including open cells, the SMP foam having first and second states; and a material composition included within the open cell, the material composition including: (a) at least one therapeutic agent, and (b) at least one of Polyvinyl alcohol (PVA), carboxymethyl cellulose, a hydrogel, or combinations thereof; wherein the at least one therapeutic agent includes at least one of a drug, a peptide, a protein, an antigen, a nucleic acid, an anesthetic, an antihistamine, antifungal agent, a vasodilator, an anti-inflammatory agent, an immunosuppressant, a growth factor, a cytokine, an interleukin, or combinations thereof.

Example 2

The apparatus of example 1, wherein the SMP foam is configured to expand from the first state to the second state when the SMP foam is plasticized at 37° C. depressing a glass transition temperature (Tg) of the SMP foam to below 25° C.

For example, "when the SMP foam is plasticized at 37° C." includes plasticization across a spectrum of temperatures. For example, plasticization may occur over a range of temperatures such as, for example, from 33° C. to 40° C. wherein 37° C. is included therein but where plasticization also occurs at 35° C. and 39° C. Further, "depressing a glass transition temperature (Tg) of the SMP foam to below 25° C." includes depressing the Tg to, for example, 24, 23, 22, 21, 20, 19, 18, 17, 16, 15, 14, 13, 12, 11, 10, 9, 8, 7, 6, 5, 4, 3, 2, 1, 0° C. and the like.

In an embodiment, when plasticized in 37° C. water, the glass transition temperature (Tg) is depressed to ~12° C. This allows for actuation when exposed to fluids at body temperature. In an embodiment the SMP foam is reticulated to make an open pore structure. Pore sizes are tunable to between 200-1500 µm. In an embodiment the SMP foam is hydrophilic. Various embodiments have tuned hydrophilicity for the SMP so the devices actuate at different rates.

As used herein, "body temperature" is meant to convey a normal body temperature range. Normal body temperature varies by person, age, activity, and time of day. The average normal body temperature is generally accepted as 98.6° F. (37° C.) however the "normal" body temperature can have a wide range, from 97° F. (36.1° C.) to 99° F. (37.2° C.). A temperature over 100.4° F. (38° C.) may indicate a fever but would still be a condition within the range of embodiments described herein.

Example 2.1

The apparatus of example 2, wherein: the SMP foam includes at least one of Hexamethylene diisocyanate (HDI), trimethyl hexamethylene diisocyanate (TMHDI), or combinations thereof; the SMP foam includes at least one of triethanolamine (TEA), hydroxypropyl ethylenediamine (HPED), or combinations thereof.

In an embodiment the foam is biodegradable.

Example 3

The apparatus of example 2, wherein: the SMP foam includes a reaction product of at least first component and a second component: the first component includes at least one of Hexamethylene diisocyanate (HDI), trimethyl hexamethylene diisocyanate (TMHDI), or combinations thereof; the second component include the SMP foam includes at least one of triethanolamine (TEA), hydroxypropyl ethylenediamine (HPED), or combinations thereof.

Example 4

The apparatus of example 2, wherein: the SMP foam includes at least one of Hexamethylene diisocyanate (HDI), trimethyl hexamethylene diisocyanate (TMHDI), or combinations thereof; the SMP foam includes at least one of Glycerol, 1,2,6-hexanetriol (HT), 3-methyl-1,5-pentanediol (MPD), 2-butyl-2-ethyl propanediol (BEP), or combinations thereof.

Example 5

The apparatus of example 2, wherein: the SMP foam includes a reaction product of at least a first component and a second component: the first component includes at least one of Hexamethylene diisocyanate (HDI), trimethyl hexamethylene diisocyanate (TMHDI), or combinations thereof; the second component includes at least one of Glycerol, 1,2,6-hexanetriol (HT), 3-methyl-1,5-pentanediol (MPD), 2-butyl-2-ethyl propanediol (BEP), or combinations thereof.

Example 6

The apparatus of example 2, wherein: the SMP foam includes at least one of Hexamethylene diisocyanate (HDI), trimethyl hexamethylene diisocyanate (TMHDI), or combinations thereof; the SMP foam includes at least one of Glycerol, 1,2,6-hexanetriol (HT), 3-methyl-1,5-pentanediol (MPD), 2-butyl-2-ethyl propanediol (BEP), or combinations thereof; the SMP foam includes at least one of 5-amino-2, 4,6-triiodoisophthalic acid (ATIPA), Iohexol, Triiodophenol, or combinations thereof.

Example 7

The apparatus of example 2, wherein: the SMP foam includes a reaction product of at least a first component, a second component, and a third component: the first component includes at least one of Hexamethylene diisocyanate (HDI), trimethyl hexamethylene diisocyanate (TMHDI), or combinations thereof; the second component includes at least one of Glycerol, 1,2,6-hexanetriol (HT), 3-methyl-1, 5-pentanediol (MPD), 2-butyl-2-ethyl propanediol (BEP), or combinations thereof; the third component includes at least one of 5-amino-2,4,6-triiodoisophthalic acid (ATIPA), Iohexol, Triiodophenol, or combinations thereof.

Example 8

The system of example 2 wherein the at least one therapeutic agent includes at least one of doxorubicin, cisplatin, paclitaxel, amoxicillin, doxycycline, cephalexin,

Example 9

A system comprising the apparatus according to any of examples 1 to 8, the system comprising a conduit that includes the SMP foam with the material composition included within the open cell.

An agent, with or without PVA, "included within the open cell" includes, for example, the agent with or without PVA completely filling a cell, partially filling a cell, or coating a strut of a cell.

In an embodiment, the PVA/agent is found throughout the SMP foam or various portions of the SMP foam. The PVA/agent deposits in small portions on struts of the SMP foam and/or forms a thin membrane on the struts. The PVA/agent may also fill the entire volume (or almost the entire volume) of the foam. In an embodiment small pieces of SMP/PVA/agent complex (e.g., beads) are injected into a wound provided those pieces are large enough to avoid entering into and being communicated within a patient's vasculature. In another embodiment, the SMP/PVA/agent combination device is attached to a bandage so the device is placed in a wound (e.g., skin cancer resection) and then pressed against the wound based on the bandage pressing against the patient.

Example 10

The system of example 9, wherein the conduit includes an additional instance of the apparatus according to any of examples 1 to 8.

For example, multiple foams may be included in a needle, sheath, or catheter. The foams may be essential the same or may be different. For example, some foams may include an agent with no PVA while other foams may include an agent within PVA. This may allow for a longer release profile. Further, the agents may or may not be the same as one another. For example, the system may be provided so a first drug is eluted during a first time period (based on its coupling to PVA or lack thereof) and a second drug (unequal in chemical composition to the first drug) is eluted during a second time period (which may overlap the first time period for a term and then not overlap the first time period for another term) in anticipation of the changing physiological characteristics of the surgical site and/or void and/or wound.

In an embodiment, a kit may be enclosed in a container. The kit may include a moderately crimped SMP foam in a sheath that holds the foam in a crimped state. The foam may have a therapeutic agent coupled to the foam via PVA or carboxymethyl cellulose or any viscosity-altering agent. The foam could be either inserted into a surgical site manually or through a catheter, sheath or cannula.

However, other embodiments require no conduit whatsoever. For example, a medical provider may simply add the foam to a void using his or her fingers or forceps.

A kit may include multiple foams with varying drug release profiles and the medical provider may select a combination of the foams to apply to the patient with the ability to tune the release profile based on the foams selected.

In an embodiment the conduit is coupled to a syringe or can be coupled to a syringe. Saline in the syringe may be used to deploy the foams into the patient.

Example 10.1

The system of example 9, wherein: the SMP foam is in the first state and has a maximum outer diameter no greater than 1.2 mm; the SMP foam is compressed in the first state and is configured to expand to the second state.

However, other embodiments may use larger embodiments wherein the SMP foam is in the first state and has a maximum outer diameter of at least 1.2, 1.5, 1.8, 2.0 mm or greater.

In an embodiment the post-crimp/compression shape is generally planar, cylindrical, spherical, and the like. These various forms may have the same or different permanent shapes (e.g., rectangular, ovular, spherical, and the like).

Example 11

The system of any of examples 9 to 10.1, wherein the conduit includes a needle that is 18 gauge or smaller.

This size may be a critical size for some applications (e.g., pediatrics, animals). For example, adding a hydrogel to a foam may limit crimping to 1.33 mm which may not fit within an 18 G needle. However, embodiments using PVA to couple the agent to the foam may be included in an 18 G needle. Any needle above the 18 G limit may not be considered an "injection" in some countries and thus could be an invasive procedure, which may increase risks and costs for the treatment. Further, such small crimped outer diameters (made possible at least in part by use of PVA) may better facilitate deployment via, for example, intravascular means that must traverse tortuous vasculature and/or other deployment routes that benefit from small form factors.

Example 12

The system according to any of examples 1 to 11, wherein the material composition directly contacts one of the cells of the SMP foam.

Example 13

The system of example 12 wherein the material composition directly contacts an inner wall of the one of the cells of the SMP foam.

In other words, the material composition is not merely in a shell of PVA that surrounds the foam. Instead, the material composition is actually included within some cells.

In an embodiment, the agent includes small molecules that are no larger than about ~900 Daltons. This may be necessary for inclusion within small celled foams that can be compressed to desired outer diameter to make them suitable for injection via needle, catheter, sheath, and the like. In other embodiments the agent may include small molecules are molecules are that are less than 1000, 800, 700, or 600 Daltons.

Applicant determined drug-loading of small molecules is difficult for foams with cells/pores that have maximum diameters of a micron or more, considering small molecules (as that term is used herein) are no larger than about ~900 Daltons. Chemotherapeutic agents typically use small molecules and such molecules can often escape such a foam (with cells on average having a maximum diameter of a micron or more) immediately after implantation. Hence, dipping such a foam in a small molecule drug solution may not enable increased drug uptake into the foam or controlled release of the drug. However, embodiments improve drug loading in the implantable SMP foam by incorporating PVA. PVA is a water-based solution that is a viscosity modulating agent. Use of PVA allowed for small molecules that are no larger than about ~900 Daltons to be retained within SMP foam open cells that have a diameter that is larger than ~900 Daltons. Use of PVA allowed for small molecules that are no larger than about ~900 Daltons to be retained within SMP foam open cells that have a diameter that is larger than 1 micron.

Example 14

The system of example 13 wherein: the one of the cells of the SMP foam is included within an interior portion of the SMP foam and is substantially surrounded by additional cells; the additional cells are included in planes that are orthogonal to each other.

Thus, an inner cell located within a middle inner portion of the foam may still include the agent within those cells (and the agent is not merely in a PVA shell around the foam). Having agent at different depths of the foam may allow for a longer delivery profile.

In an embodiment small molecule agents (e.g., acriflavine) may be located within PVA and within the foam but not necessarily within the PVA. As a result, the agent may be released at different times. For example, the agent not included in the PVA but still within the foam may release after agent that is included in PVA but not necessarily within the foam. Such PVA encased agent may be on the outer surface of the foam and held in place by PVA that couple the agent to the foam. Therefore, even though a SMP foam may not necessarily be able to take up as much agent without PVA as is the case with, the combination of foam having portions with PVA encased agent and portions without PVA agents may be beneficial.

An embodiment includes a SMP coated with PVA that has bimodal or trimodal release kinetics such that there is an immediate release of the agents from the PVA and delayed bolus(es) of the same or different therapeutic from direct loading in the SMP polymer network.

Embodiments may include a first agent included in a PVA shell that surrounds the foam and a second agent included in PVA and within cells of the foam. The first and second agents may have the same or different chemical compositions. With this arrangement the first agent may be eluted first followed by elution of the second agent.

Embodiments may include a first agent included in a PVA shell that surrounds the foam, a second agent included in PVA (or not included in PVA) and within outer cells of the foam, and a third agent included in PVA (or not included in PVA) and within inner cells of the foam. The first, second agents, and third agents may have the same or different chemical compositions. With this arrangement the first agent may be eluted first followed by elution of the second agent followed by elution of the third agent.

Example 15

The system according to any of examples 1 to 11, wherein the therapeutic agent is encapsulated by at least one of a polymer, liposome, a micelle particle, or combinations thereof.

Embodiments may include, for example, tertiary delayed release of drugs via triggered mechanisms (e.g., ultrasound breaking microbeads with an additional drug load) or automatic mechanisms (e.g., moderately bound drugs that release with degradation). For instance, in some embodiments a portion of agent may be included within the foam in an unencapsulated state while another portion of the foam may be included in the foam in an encapsulated state. The initial release of the agent may be from the unencapsulated agent followed by a later release from the encapsulated agent once the encapsulated agent is subjected to sufficient energy (e.g., ultrasound). The unencapsulated agent and encapsulated agent may be different agents or the same agents.

Such an embodiment may have an advantage over systems that use a foam and a hydrogel, with the hydrogel loaded with drug. Such a foam may be prone to immediate dissolution of the hydrogel upon contact with physiological environment. In such a case drug release can be better controlled by loading either free drug or drug encapsulated within polymeric, liposome, or micelle-like particles.

Drug release profiles can be modulated depending on the desired therapeutic effect. For example, using drug encapsulated nanoparticles instead of a free drug may change the delivery profile. Drug-encapsulated vehicles (including microparticles and nanoparticles and hydrogels) can enable delayed sustained release once the particles are released from the foam. Thus, the drug-eluting SMP foams can facilitate short-term and long-term drug delivery depending on the type of cargo and PVA used. The amount of drug release can also be optimized based on the stock concentration of the drug.

Example 16

The system of example 15 wherein: the encapsulated therapeutic agent is included in the at least one of Polyvinyl alcohol (PVA), carboxymethyl cellulose, or combinations thereof; the at least one of Polyvinyl alcohol (PVA), carboxymethyl cellulose, or combinations thereof is between a wall of a cell of the SMP foam and the encapsulated therapeutic agent such that the encapsulated therapeutic agent does not directly contact the wall.

Example 17

A method comprising: forming a void in a patient's tissue; locating the apparatus according to any of examples 1 to 10.1 or 12 to 16 within the void.

Example 18

A method comprising: forming a void in a patient's tissue; locating a distal tip of the conduit according to any of examples 9 to 11 within the void while the conduit includes the apparatus according to any of examples 1 to 16; moving the apparatus from within the conduit to within the void.

Example 19

A method comprising: forming a composition including: (a) at least one therapeutic agent, (b) dimethyl sulfoxide (DMSO), and (c) at least one of Polyvinyl alcohol (PVA), carboxymethyl cellulose, or combinations thereof; applying the composition to a shape memory polymer (SMP) foam including open cells to form a combination of the SMP foam and the composition; drying the combination at a pressure that is less than 1,013.25 mbar; programming the SMP foam to have a primary shape, and then forming the SMP foam into a stable secondary shape, wherein the SMP foam is configured to be controllably actuated to recover the primary shape; wherein the SMP foam in the secondary shape includes the SMP foam, the at least one therapeutic agent, the DMSO, and the at least one of PVA, carboxymethyl cellulose, or combinations thereof; wherein the at least one therapeutic agent includes at least one of a drug, a peptide, a protein, an antigen, a nucleic acid, an anesthetic, an antihistamine, antifungal agent, a vasodilator, an anti-inflammatory agent, an immunosuppressant, a growth factor, a cytokine, an interleukin, or combinations thereof.

However, in other embodiments a substitute for DMSO may be used, such as ethanol, salt-based solvents, and water-based solvents, instead of or in addition to DMSO. In other embodiments, the DMSO or its replacement may be removed during the manufacturing process such that the DMSO or its replacement is no longer included in the SMP foam that is in the secondary shape. Such a solvent (e.g., DMSO) may be included within the therapeutic agent (anti-cancer drug) itself.

In some embodiments the agent and PVA may be combined and added to the foam simultaneously while in other embodiments they may be added to the foam separately.

In an embodiment, the agent is loaded into the foam by solvent swelling with DMSO. Then the foam with agent are loaded into a PVA hydrogel that surrounds the foam to form a hydrogel and foam composite.

A method includes the following: (1) the SMP foam/PVA/agent device is heated above its Tg and held in the desired geometry for packaging; (2) the device is cooled below its Tg to program the packaged shape into the device; (3) the device is sterilized under EtO sterilization and packaged and stored at temperatures less than 30 degrees Celsius; (4) to apply the foam, the foam is removed from the package and inserted anywhere within the patient; (5) the foam plasticizes at body temperature to expand and fill some or all of a void; and (6) drug elution occurs over time.

Example 20

A porous, biodegradable/bioresorbable, shape memory polymer (SMP) foam that is used to fill voids in tissue left by surgery or other procedures related to removing cancerous, pre-cancerous or other tissues from patients preventing metastasis.

Example 21

The SMP foams of example 20 that are loaded with and elute anti-cancer therapeutic(s) (single therapeutic of combination).

Example 22

Drug-loaded spherical foams can also be injected into the blood vessels that feed into the tumor potentially increasing the drug concentration at the tumor site and minimizing the side effects from damaging normal tissues.

Examples of therapeutics that can be loaded in the SMP foams include small molecules used as anti-cancer agents including, but not limited to, doxorubicin, cisplatin, and paclitaxel, antigens, and peptides. Other examples of therapeutics include antibiotics including, but not limited to, amoxicillin, doxycycline, and cephalexin that are used to treat infectious diseases can also be loaded onto the foams. Other therapeutic agents include antigens, proteins, and nucleic acids can also be loaded onto the foams.

Cargo loaded onto the foam can also include local anesthetics, antihistamines, antifungal agents, vasodilators, anti-inflammatory agents, and immunosuppressants.

Examples of carrier materials that are loaded with the drugs and coated on and in the SMP foams include, PVA, CMC, hydrogel, and other polymer-based nanoparticles to enable different release profiles.

Example 1a

An apparatus comprising: a shape memory polymer (SMP) foam including an open cell and additional open cells, the SMP foam having first and second states; and a material composition included in the open cell, the material composition including: (a) a therapeutic agent, and (b) at least one of Polyvinyl alcohol (PVA), carboxymethyl cellulose, or combinations thereof; wherein the therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof.

While this example lists at least one of PVA, carboxymethyl cellulose, or combinations thereof, other embodiments may include viscosity increasing agents such as (depending on the application for the embodiment) acacia, agar, alamic acid, aluminum monostearate, attapulgite, bentonite, carbomer, carboxymethyl cellulose calcium, carboxymethyl cellulose sodium, carrageenan, cellulose, dextrin, gelatin, gellan gum, guar gum, hydroxyethyl cellulose, hydroxypropyl cellulose, Hypromellose, magnesium aluminum silicate, maltodextrin, methyl cellulose, microcrystalline cellulose, pectin, polyethylene oxide, povidone, propylene glycol alginate, silicon dioxide, sodium alginate, starch (corn, potato, tapioca, wheat), tragacanth, xanthum gum, or combinations therefrom.

In an embodiment the material composition will fluoresce to help a medical care provider monitor agent release (via imaging) over time.

Another Version of Example 1a

An apparatus comprising: a shape memory polymer (SMP) foam including an open cell and additional open cells, the SMP foam having first and second states; and a fluorescent material composition included in the open cell, the material composition including: (a) a therapeutic agent, and (b) at least one of Polyvinyl alcohol (PVA), carboxymethyl cellulose, or combinations thereof; wherein the therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof.

Another Version of Example 1a

An apparatus comprising: a shape memory polymer (SMP) foam including an open cell and additional open cells, the SMP foam having first and second states; and a material composition included in the open cell, the material composition including: (a) a therapeutic agent, and (b) at least one of Polyvinyl alcohol (PVA), carboxymethyl cellulose, or combinations thereof; wherein the therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof; wherein the SMP foam is configured to expand into an irregularly shaped tissue void when the SMP foam expands from the first state to the second state to thereby physically press the SMP foam directly against a margin of the irregularly shaped tissue void.

Another Version of Example 1a

An apparatus comprising: a shape memory polymer (SMP) foam including an open cell and additional open cells, the SMP foam having first and second states; and a material composition included in the open cell, the material composition including: (a) a therapeutic agent, and (b) at least one of Polyvinyl alcohol (PVA), carboxymethyl cellulose, or combinations thereof; wherein the therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof; wherein the SMP foam is configured to expand into an irregularly shaped tissue void when the SMP foam expands from the first state to the second state to thereby conform the SMP foam to an irregularly shaped margin of the irregularly shaped tissue void.

Embodiments addressed herein provide: (1) precise plugging of post-surgery tissue voids, and/or (2) high loading and controlled release of chemotherapeutic agents to prevent cancer recurrence and metastasis. Embodiments indicate: (1) drug loading was improved by ~80% with increased PVA concentration, and/or (2) delayed burst and sustained release of drugs were achieved based on PVA concentrations used.

As a result, embodiments include a drug-loaded SMP foam that enables increased chemotherapeutic drug uptake while effectively sealing a tissue void. This provides a well-rounded solution to counter the occurrence of metastasis after tumor resection.

Another Version of Example 1a

An apparatus comprising: a shape memory polymer (SMP) foam including an open cell and additional open cells, the SMP foam having first and second states; and a material composition included in the open cell, the material composition including: (a) a therapeutic agent, and (b) at least one viscosity-inducing agent; wherein the therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof.

Example 2a

The apparatus of example 1a, wherein the SMP foam is configured to expand from the first state to the second state when the SMP foam is plasticized at 37° C. depressing a glass transition temperature (Tg) of the SMP foam to below 25° C.

Example 3a

The apparatus of example 2a, wherein: the SMP foam includes a reaction product of at least a first component and a second component: the first component includes at least one of Hexamethylene diisocyanate (HDI), trimethyl hexamethylene diisocyanate (TMHDI), or combinations thereof; the second component includes at least one of triethanolamine (TEA), hydroxypropyl ethylenediamine (HPED), or combinations thereof.

Example 4a

The apparatus of example 2a, wherein: the SMP foam includes a reaction product of at least a first component and a second component: the first component includes at least one of Hexamethylene diisocyanate (HDI), trimethyl hexamethylene diisocyanate (TMHDI), or combinations thereof; the second component includes at least one of Glycerol, 1,2,6-hexanetriol (HT), 3-methyl-1,5-pentanediol (MPD), 2-butyl-2-ethyl propanediol (BEP), or combinations thereof.

Example 5a

The apparatus of example 2a, wherein: the SMP foam includes a reaction product of at least a first component, a second component, and a third component: the first component includes at least one of Hexamethylene diisocyanate (HDI), trimethyl hexamethylene diisocyanate (TMHDI), or combinations thereof; the second component includes at least one of Glycerol, 1,2,6-hexanetriol (HT), 3-methyl-1, 5-pentanediol (MPD), 2-butyl-2-ethyl propanediol (BEP), or combinations thereof; the third component includes at least one of 5-amino-2,4,6-triiodoisophthalic acid (ATIPA), Iohexol, Triiodophenol, or combinations thereof.

Example 6a

The apparatus according to any of examples 1a to 5a wherein the therapeutic agent includes at least one of doxorubicin, cisplatin, paclitaxel, amoxicillin, doxycycline, cephalexin, or combinations thereof.

Example 7a

The apparatus according to any of examples 1a to 6a comprising a conduit, the conduit including the SMP foam.

Example 8a

The apparatus of example 7a, wherein the conduit includes an additional instance of the SMP foam.

Another Version of Example 8a

The apparatus of example 7a, wherein: the conduit includes another SMP foam including another open cell, the another SMP foam having first and second states; and another material composition included in the another open cell, the another material composition including: (a) another therapeutic agent, and (b) another at least one of PVA, carboxymethyl cellulose, or combinations thereof; wherein the another therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof; wherein the material composition includes a first amount of the at least one of PVA, carboxymethyl cellulose, or combinations thereof; wherein the another material composition includes a second amount of the another at least one of PVA, carboxymethyl cellulose, or combinations thereof; wherein the first amount is unequal to the second amount.

Another Version of Example 8a

The apparatus of example 7a, wherein: the conduit includes another SMP foam including another open cell, the another SMP foam having first and second states; and another material composition included in the another open cell, the another material composition including: (a) another therapeutic agent, and (b) another at least one of PVA, carboxymethyl cellulose, or combinations thereof; wherein the another therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof; wherein the material composition includes a first amount of the therapeutic agent; wherein the another material composition includes a second amount of the another therapeutic agent; wherein the first amount is unequal to the second amount.

Example 9a

The apparatus of example 7a, wherein: the SMP foam is in the first state and has a maximum outer diameter no greater than 1.2 mm; the SMP foam is compressed in the first state and is configured to expand to the second state.

For instance, the ability to crimp to such a small diameter may be extremely difficult if a hydrogel were used instead of, for example, PVA.

Example 10a

The apparatus of example 9a wherein the conduit includes a needle that is 18 gauge or smaller.

However, other embodiments may not require a needle or conduit. For example, a medical care provider may wish to simply take SMP foam described herein and apply it directly to a tissue (e.g., tumor resection) using his or her hands.

Example 11a

The apparatus of example 9a wherein: the open cell includes a maximum diameter of at least 50 microns; the therapeutic agent is not larger than 900 Daltons.

In other embodiments the maximum diameter of the open cell is between 50 microns and 2 mm. In other embodiments the maximum diameter of the open cell is less than 2 mm but greater than 50, 75, 100, 125, 150, 175, or 200 microns.

Example 12a

The apparatus of example 9a wherein: the open cell includes at least one of a strut and an inner wall; and the material composition directly contacts the at least one of a strut and an inner wall.

Example 13a

The apparatus of example 12a wherein the open cell: is included within an interior portion of the SMP foam; is substantially surrounded by the additional open cells; and does not directly contact an outer surface of the SMP foam.

Example 14a

The apparatus according to any of examples 1a to 13a, wherein the therapeutic agent is encapsulated by at least one of a polymer, a liposome, a micelle particle, or combinations thereof.

Example 15a

The apparatus of example 14a wherein: the encapsulated therapeutic agent is included in the at least one of PVA, carboxymethyl cellulose, or combinations thereof; the at least one of PVA, carboxymethyl cellulose, or combinations thereof is between a wall of a cell of the SMP foam and the encapsulated therapeutic agent such that the encapsulated therapeutic agent does not directly contact the wall.

Example 16a

The apparatus of example 1a comprising a coating, wherein: the open cell includes a strut; the coating is on the strut; and the coating includes the material composition.

Example 17a

The apparatus of example 16a wherein an interior portion of the strut includes at least one of the therapeutic agent, an additional therapeutic agent, or combinations thereof.

See, for example, FIG. 4. The agent (e.g., drug) may be incorporated into the strut interior via a solvent (such as DMSO). Based on chemistry of the foam in certain embodiments (e.g., examples 3a to 5a) the PVA coating cannot carry the agent into the SMP strut by itself. Without any solvent, the agent stays in the carrier coating. Thus, use of a solvent may help incorporate an agent into the strut (instead of just on the strut).

A method includes loading an agent into the strut (or wall or general infrastructure of SMP foam cell) in a different step from loading an agent onto the strut. For example, first one load drug A into the SMP strut using a solvent. Second, one loads drug B (or more of drug A) onto the strut surface with a carrier coating.

Another version of Example 17a. The apparatus of example 16a wherein: (a) an interior portion of the strut when the SMP foam is in the first state includes at least one of the therapeutic agent, an additional therapeutic agent, or combinations thereof, and (b) the interior portion of the strut when the SMP foam is in the second state includes the at least one of the therapeutic agent, an additional therapeutic agent, or combinations thereof.

Example 18a

The apparatus of example 16a wherein: the therapeutic agent of the coating is configured to elute from the SMP foam and into a patient tissue during a first period of time; an interior portion of the strut includes at least one of the therapeutic agent, an additional therapeutic agent, or combinations thereof that is configured to elute from the SMP foam and into the patient tissue during a second period of time; the second period of time occurs at least one day after the first period of time.

For example, drug A in the coating may elute into the resection margin tissue over a first time window (e.g., 1-48 hours) while drug B (or drug A or drugs A and B) in the strut interior elutes into the tissue later (e.g., after 48 hours or after 1 week). This may occur due to the drug in the strut interior eluting from an intact strut. However, this may also occur because the strut is biodegradable and degrades over time. As the strut degrades any drug within its interior will elute into the surrounding tissues.

The above scenario addresses an example of a "dual release" mechanism whereby a drug (drug A) is released from the coating (first route of the dual release) and a drug (drug A, B, or A and B) is released from within a strut or cell infrastructure component (second route of the dual release).

In an embodiment, the drug (whether it be in the coating or in a strut) may be hydrophilic. This is notable because hydrophilic drugs may not dissolve in organic solvents. Doxorubicin and Acriflavine are soluble in both DMSO and water. The presence of DMSO (even trace amounts) in the foam helps in expansion of the foam (resulting in more drug penetrating the foam's core). A solvent such as an organic solvent may be used to load a hydrophilic agent into the interior of a strut or cell wall having the chemistry of examples 3a-5a. Such solvents include, for example, DMSO, methanol, ethanol, propanol, dimethyl sulphoxide (DMSO), N,N-dimethyl formamide (DMF), and glycerol.

Some such solvents may be inappropriate for certain applications due to the interaction with tissue if the solvent remains in the SMP foam.

Example 19a

The apparatus according to any of examples 17a-18a wherein the interior portion of the strut includes the additional therapeutic agent.

Example 20a

The apparatus according to any of examples 17a-19a wherein the interior portion of the strut does not include the at least one of PVA, carboxymethyl cellulose, or combinations thereof.

Another Version of Example 20a

The apparatus according to any of examples 17-19 wherein: the interior portion of the strut does not include the at least one of PVA, carboxymethyl cellulose, or combinations thereof; and the material composition is not cross-linked around the strut.

In an embodiment the open cell includes a maximum diameter of at least 50 microns and the therapeutic agent is not larger than 900 Daltons. However, without crosslinking of the material composition around the strut, a delayed or sustained release of the agent is made more difficult. However, the use of a carrier polymer that increases viscosity may help counter the lack of material composition crosslinking to enable sustained agent release.

In an embodiment the material composition is not chemically bonded (e.g., covalent bonding) to the foam. Instead, the material composition is physically included within the material composition. This avoids possibly damaging the agent in any manner.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. An apparatus comprising:
a shape memory polymer (SMP) foam including an open cell and additional open cells, the SMP foam having first and second states; and
a material composition included in the open cell, the material composition including: (a) a therapeutic agent, and (b) at least one of Polyvinyl alcohol (PVA), carboxymethyl cellulose, or combinations thereof;
wherein the therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof
wherein: (a) the SMP foam includes a reaction product of at least a first component and a second component, (b) the first component includes at least one of Hexamethylene diisocyanate (HDI), trimethyl hexamethylene diisocyanate (TMHDI), or combinations thereof, and (c) the second component includes at least one of Glycerol, 1,2,6-hexanetriol (HT), 3-methyl-1,5-pentanediol (MPD), 2-butyl-2-ethyl propanediol (BEP), or combinations thereof.

2. The apparatus of claim 1, wherein the SMP foam is configured to expand from the first state to the second state when the SMP foam is plasticized at 37° C. depressing a glass transition temperature ($T_g$) of the SMP foam to below 25° C.

3. The apparatus of claim 2, wherein:
the SMP foam includes a reaction product of at least the first component, the second component, and a third component;
the third component includes at least one of 5-amino-2,4,6-triiodoisophthalic acid (ATIPA), Iohexol, Triiodophenol, or combinations thereof.

4. The apparatus of claim 1 wherein the therapeutic agent includes at least one of doxorubicin, cisplatin, paclitaxel, amoxicillin, doxycycline, cephalexin, or combinations thereof.

5. The apparatus of claim 1 comprising a conduit, the conduit including the SMP foam.

6. The apparatus of claim 5, wherein:
the conduit includes another SMP foam including another open cell, the another SMP foam having first and second states; and
another material composition included in the another open cell, the another material composition including: (a) another therapeutic agent, and (b) another at least one of PVA, carboxymethyl cellulose, or combinations thereof;
wherein the another therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof;
wherein the material composition includes a first amount of the at least one of PVA, carboxymethyl cellulose, or combinations thereof;
wherein the another material composition includes a second amount of the another at least one of PVA, carboxymethyl cellulose, or combinations thereof;
wherein the first amount is unequal to the second amount.

7. The apparatus of claim 5, wherein:
the SMP foam is in the first state and has a maximum outer diameter no greater than 1.2 mm;
the SMP foam is compressed in the first state and is configured to expand to the second state.

8. The apparatus of claim 7 wherein the conduit includes a needle having an inner diameter no wider than an inner diameter of an 18 gauge needle.

9. The apparatus of claim 7 wherein:
the open cell includes a maximum diameter of at least 50 microns;
the therapeutic agent is not larger than 900 Daltons.

10. The apparatus of claim 7 wherein:
the open cell includes at least one of a strut and an inner wall; and
the material composition directly contacts the at least one of a strut and an inner wall.

11. The apparatus of claim 10 wherein the open cell:
is included within an interior portion of the SMP foam;
is substantially surrounded by the additional open cells; and
does not directly contact an outer surface of the SMP foam.

12. The apparatus of claim 1, wherein the therapeutic agent is encapsulated by at least one of a polymer, a liposome, a micelle particle, or combinations thereof.

13. The apparatus of claim 12 wherein:
the encapsulated therapeutic agent is included in the at least one of PVA, carboxymethyl cellulose, or combinations thereof;
the at least one of PVA, carboxymethyl cellulose, or combinations thereof is between a wall of a cell of the SMP foam and the encapsulated therapeutic agent such that the encapsulated therapeutic agent does not directly contact the wall.

14. The apparatus of claim 1 comprising a coating, wherein:
the open cell includes a strut;
the coating is on the strut; and
the coating includes the material composition.

15. The apparatus of claim 14 wherein:
the therapeutic agent of the coating is configured to elute from the SMP foam and into a patient tissue during a first period of time;
an interior portion of the strut includes at least one of the therapeutic agent, an additional therapeutic agent, or combinations thereof that is configured to elute from the SMP foam and into the patient tissue during a second period of time;
the second period of time occurs at least one day after the first period of time.

16. The apparatus of claim 14 wherein an interior portion of the strut includes at least one of the therapeutic agent, an additional therapeutic agent, or combinations thereof.

17. The apparatus of claim 16 wherein the interior portion of the strut includes the additional therapeutic agent.

18. The apparatus of claim 16 wherein:
the interior portion of the strut does not include the at least one of PVA, carboxymethyl cellulose, or combinations thereof; and
the material composition is not crosslinked around the strut.

19. An apparatus comprising:
a shape memory polymer (SMP) foam including an open cell and additional open cells, the SMP foam having first and second states; and
a material composition included in the open cell, the material composition including: (a) a therapeutic agent, and (b) at least one of Polyvinyl alcohol (PVA), carboxymethyl cellulose, or combinations thereof;
wherein the therapeutic agent includes at least one of a drug, a peptide, a protein, an antigen, a nucleic acid, an anesthetic, an antihistamine, an antifungal agent, a vasodilator, an anti-inflammatory agent, an immunosuppressant, a growth factor, a cytokine, an interleukin, or combinations thereof
wherein: (a) the SMP foam includes a polymer that comprises polymerized first and second monomers, (b) the first monomers including at least one of Hexamethylene diisocyanate (HDI), trimethyl hexamethylene diisocyanate (TMHDI), or combinations thereof, and (c) the second monomers including at least one of Glycerol, 1,2,6-hexanetriol (HT), 3-methyl-1,5-pentanediol (MPD), 2-butyl-2-ethyl propanediol (BEP), or combinations thereof.

20. The apparatus of claim 19, wherein the SMP foam is configured to expand from the first state to the second state when the SMP foam is plasticized at 37° C. depressing a glass transition temperature ($T_g$) of the SMP foam to below 25° C.

21. The apparatus of claim 19 comprising a coating, wherein:
the open cell includes a strut;
the coating is on the strut;
the coating includes the material composition;
the therapeutic agent of the coating is configured to elute from the SMP foam and into a patient tissue during a first period of time;
an interior portion of the strut includes at least one of the therapeutic agent, an additional therapeutic agent, or combinations thereof that is configured to elute from the SMP foam and into the patient tissue during a second period of time;
the second period of time occurs at least one day after the first period of time.

* * * * *